United States Patent [19]

Wright et al.

[11] 4,374,246
[45] Feb. 15, 1983

[54] 1-N-[(1-CARBOXY-3-PHENYLPROPYL)-GLYCYL]-1,2,3,4-TETRAHYDROQUINOLINE-2-CARBOXYLIC ACID COMPOUNDS

[75] Inventors: George C. Wright; Ronald E. White, both of Norwich, N.Y.

[73] Assignee: Norwich Eaton Pharmaceuticals, Inc., Norwich, N.Y.

[21] Appl. No.: 275,064

[22] Filed: Jun. 18, 1981

[51] Int. Cl.³ .................. C07D 215/12; C07D 215/16
[52] U.S. Cl. .................................... 546/156; 424/158
[58] Field of Search ............................... 546/156, 146

[56] References Cited

U.S. PATENT DOCUMENTS 3,514,465  5/1970  Posselt et al.
4,303,583  12/1981  Kim et al. ........................ 260/239.3

FOREIGN PATENT DOCUMENTS 12845  7/1980  European Pat. Off. ............ 546/157
18104  10/1980  European Pat. Off. ............ 546/157
2448533  2/1980  France ............................. 546/146

Primary Examiner—Donald G. Daus
Assistant Examiner—G. Hendricks
Attorney, Agent, or Firm—Anthony J. Franze

[57] ABSTRACT

Compounds of the formula:

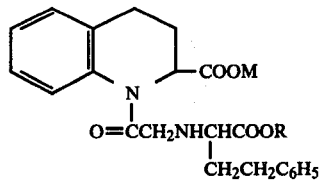

wherein
  M is hydrogen or sodium and
  R is hydrogen or ethyl
are useful as angiotensin I converting enzyme inhibitors.

3 Claims, No Drawings

1-N-[(1-CARBOXY-3-PHENYLPROPYL)GLYCYL]-1,2,3,4-TETRAHYDROQUINOLINE-2-CARBOXYLIC ACID COMPOUNDS

This invention is concerned with 1-[N-(1-carboxy-3-phenylpropyl)glycyl]-1,2,3,4-tetrahydroquinoline-2-carboxylic acid compounds of the formula:

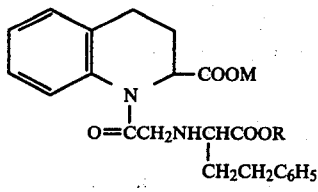

wherein
M is hydrogen or sodium and
R is hydrogen or ethyl

The compounds are potent inhibitors of the enzyme responsible for converting the decapeptide angiotensin I to the octapeptide angiotensin II. Angiotensin II is the powerful pressor agent implicated as the causative agent in some form of hypertension.

Of late, it has been recognized that a substance capable of interrupting the pathway whereby angiotensin II is produced, viz., the conversion hereabove referred to, presents a useful and effective means of combatting hypertension associated with that pressor agent.

It has been discovered that the compounds of this invention are possessed of noteworthy activity in inhibiting angiotensin I converting enzyme. Thus, in in vitro techniques designed to evince such activity these compounds are highly effective. For example, they inhibit the pure converting enzyme isolated from rabbit lung tissue at levels from about 0.126 to 40.34 μm. They are, therefore, notable angiotensin I converting enzyme inhibitors.

The compounds of this invention are not limited to in vitro manifestations of their converting enzyme inhibiting propensity. Upon oral administration, a dose-dependent antihypertensive effect in acute aortic coarctation hypertension rats is elicited. Oral dosages of from 10 mg/kg to 200 mg/kg administered as a suspension in 0.5% Methocel solution achieve a reduction of from 20-30 mm Hg in mean arterial blood pressure in such rats.

The compounds of this invention can be composed in a variety of dosage forms such as tablets, capsules, solutions and the like for convenient administration employing classical excipients and adjuvants with which there is no incompatability. Such dosage forms contain from 10 to 500 mg of a compound of formula (I) or a salt thereof in a unit dosage form in accordance with accepted pharmaceutical practice.

In order that this invention may be readily available to and understood by those skilled in the art the following examples represent now preferred methods for the preparation thereof.

EXAMPLE I 1,2,3,4-Tetrahydro-1-[2-[1,3-dihydro-1,3-dioxo-2H-isoindol-2-yl]acetyl]quinoline-2-carboxylic acid A stirred mixture of 1,2,3,4-tetrahydroisoquinoline-2-carboxylic acid (75.0 g, 0.351 mole) and H$_2$O (260 ml) was cooled on an ice bath. NaOH (28.03 g, 0.702 mole) dissolved in H$_2$O (250 ml) was added and the solution cooled on an ice bath to 0°–5°. NaOH (14.04 g, 0.351 mole) dissolved in H$_2$O (150 ml) and N-phthaloylglycine acid chloride (78.5 g, 0.351 mole) dissolved in tetrahydrofuran (450 ml) were added dropwise simultaneously over 4.0 hours keeping the temperature 0°–5°. The solution was allowed to warm slowly and stirred under ambient conditions (25°) overnight. The resulting mixture was cooled on an ice bath to 5°–10° and acidified with conc. HCl dropwise to a pH of 1–2. This mixture was stirred with ether (2000 ml) on an ice bath for 1.0 hour. The resulting solid was collected by filtration, washed with ether (500 ml) and air dried to give 65.5 g (0.180 mole). The filtrate and washing were combined and the ethereal layer separated. The ethereal layer was filtered through MgSO$_4$ and concentrated under reduced pressure to an oily residue. This residue was triturated in abs. ethanol (100 ml) to form a solid. This solid was collected by filtration, washed with abs. ethanol (50 ml) and air dried to give 9.7 g (0.027 mole) of title product. Combined yield 75.2 g (0.206 mole, 59% yield).

Anal. Calcd. for C$_{20}$H$_{10}$N$_2$O$_5$: C, 65.93; H, 4.43; N, 7.69; Found: C, 65.74; H, 4.42; N, 7.50.

EXAMPLE II

Glycyl-1,2,3,4-tetrahydroquinoline-2-carboxylic Acid

To a stirred mixture of the compound of Example I (75.2 g, 0.206 mole) and methanol (400 ml) was added 85% N$_2$H$_4$.H$_2$O (12.7 ml, 0.220 mole) dissolved in methanol (30 ml) dropwise over 0.5 hours. After stirring under ambient conditions for 15 minutes, the solution was heated to reflux. Reflux was maintained for 6.0 hours, then allowed to cool overnight at 0°. The crystalline solid was collected, washed with methanol (50 ml) and air dried to give 68.0 g. This solid (68.0 g) was stirred in H$_2$O (175 ml) for 2.0 hours, then filtered. The insoluble solid was washed with H$_2$O (2×5 ml). The filtrate and washing were combined and concentrated under high vacuum to ⅓ its volume. This was diluted with abs. ethanol (150 ml) and concentrated under reduced pressure to a solid residue. This residue was triturated in abs. ethanol (100 ml), collected by filtration and air dried to give 25.2 g. This crude solid was stirred in ethanol/H$_2$O (9:1, 300 ml) for 2.0 hours, filtered and air dried to give 18.6 g (0.079 mole, 38% yield) of title product.

Anal. Calcd. for C$_{12}$H$_{14}$N$_2$O$_3$: C, 61.53; H, 6.02; N, 11.96; Found: C, 62.23; H, 6.10; N, 11.83.

EXAMPLE III

1-[N-(1-Carboxy-3-phenylpropyl)glycyl]-1,2,3,4-tetrahydroquinoline-2-carboxylic Acid Tetartohydrate A mixture of 2-oxo-4-phenylbutanoic acid (14.2 g, 0.0796 mole) and H$_2$O (50 ml) was adjusted to pH 6.9 by the dropwise addition of 50% NaOH (the temperature increased from 20° to 26°). Then the compound of Example II (3.40 g, 0.0145 mole) was added and the mixture was stirred for 10 minutes giving a solution at pH 6.25. A solution of sodium cyanoborohydride (2.80 g, 0.0450 mole) and H$_2$O (50 ml) was added dropwise over a period of 35 minutes giving a solution at pH 7.95. The reaction was stirred for 16 hours giving a solution of pH 8.45. The solution was diluted with methanol (200 ml), cooled to 20°, and Dowex 50W-X4 (100–200 mesh) cation exchange resin (340 ml) was added in portions over 20 minutes at 20°–24°. The mixture was stirred for 1½ hours and added to a 62×6 cm column containing 200 ml of Dowex 50W-X4 resin. The resin was washed with 50% methanol (4 l) and H$_2$O (2 l). The product was eluted with 2% pyridine (3 l) and 100 ml fractions were collected. The final 18 fractions were combined and stripped of solvent in vacuo, keeping the water bath temperature below 20°. The residue was washed in CHCl$_3$ (50 ml) and the product was collected by filtration; m.p. 124°–127°, yield: 3.4 g (59%).

Anal. Calcd. for C$_{22}$H$_{24}$N$_2$O$_5$·¼H$_2$O: C, 65.90; H, 6.16; N, 6.99; H$_2$O, 1.1; Found: C, 65.65; H, 5.82; N, 6.82; H$_2$O, 3.7.

EXAMPLE IV

1-[N-[1-Ethoxycarbonyl)-3-phenylpropyl]glycyl]-1,2,3,4-tetrahydroquinoline-2-carboxylic Acid Sodium Salt Tetartohydrate A mixture of the compound of Example II (1.70 g, 0.00725 mole) and 50% ethanol (30 ml) was stirred for 10 minutes at room temperature. The ethyl 2-oxo-4-phenylbutyrate (8.21 g, 0.0398 mole) was added, followed by the dropwise addition of sodium cyanoborohydride (1.40 g, 0.0225 mole) in 50% ethanol (25 ml) over 70 minutes. The solution was stirred for 23 hours and the solvent was removed in vauco. The residue was dissolved in H$_2$O (50 ml) to give a solution at pH 7.65. Then 5% NaHCO$_3$ was added until pH 8.41 was achieved. The aqueous phase was extracted with CHCl$_3$ (2×50 ml), the organic phase was dried over Na$_2$SO$_4$ and Darco, filtered, and the filtrate was stripped of solvent under reduced pressure. The residue was dissolved in CCl$_4$ (30 ml), stirred over Na$_2$SO$_4$ and Darco, filtered, and the filtrate was stripped of solvent under reduced pressure. The residue was shaken in H$_2$O (75 ml) and extracted with cyclohexane 3×30 ml). The water phase was stripped of solvent in vacuo leaving a solid product, yield: 1.5 g (46%); m.p. 66°–83°.

Anal. Calcd. for C$_{24}$H$_{27}$N$_2$NaO$_5$·¼H$_2$O: C, 63.92; H, 6.15; N, 6.21; Na, 5.10; H$_2$O, 1.0; Found: C, 63.62; H, 6.02; N, 6.09; Na, 4.58, 4.66; H$_2$O, 1.04, 1.22.

What is claimed is:

1. A compound of the formula:

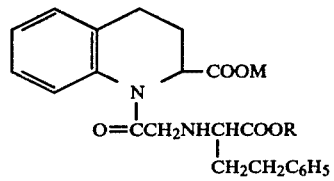

wherein
M is hydrogen or sodium and
R is hydrogen or ethyl.

2. The compound 1-[N-1-carboxy-3-phenylpropyl)-glycyl]-1,2,3,4-[tetrahydroisoquinoline]tetrahydroquinoline-2-carboxylic acid.

3. The compound 1-[N-[1-(ethoxycarbonyl)-3-phenylpropyl]glycyl]-1,2,3,4-tetrahydroquinoline-2-carboxylic acid sodium salt.

* * * * *